United States Patent [19]

François et al.

[11] Patent Number: 6,054,462
[45] Date of Patent: *Apr. 25, 2000

[54] INTRANASAL ANTIMIGRAINE COMPOSITIONS

[75] Inventors: Marc Karel Jozef François, Kalmthout; Roger Carolus Augusta Embrechts, Oud-Turnhout, both of Belgium; Lisbeth Illum, Nottingham, United Kingdom

[73] Assignee: Janssen Pharmaceutica, N.V., Belgium

[*] Notice: This patent issued on a continued prosecution application filed under 37 CFR 1.53(d), and is subject to the twenty year patent term provisions of 35 U.S.C. 154(a)(2).

[21] Appl. No.: 08/963,432

[22] Filed: Nov. 3, 1997

Related U.S. Application Data

[63] Continuation of application No. 08/718,529, Oct. 8, 1996, abandoned.

[30] Foreign Application Priority Data

Apr. 13, 1994 [EP] European Pat. Off. ............ 94.200.998

[51] Int. Cl.⁷ ........................ A61K 31/505; A61K 47/36
[52] U.S. Cl. ............................................. 514/275; 514/929
[58] Field of Search ...................... 514/275, 929

[56] References Cited

U.S. PATENT DOCUMENTS

| 4,929,722 | 5/1990 | Partain, III et al. ...................... 536/20 |
| 4,946,870 | 8/1990 | Partain, III et al. ..................... 514/777 |
| 5,300,494 | 4/1994 | Brode, II et al. ........................... 514/55 |
| 5,541,180 | 7/1996 | Van Lommen et al. ................. 514/218 |

FOREIGN PATENT DOCUMENTS

| 0 408 069 A2 | 1/1991 | European Pat. Off. . |
| WO 90/09780 | 9/1990 | WIPO .............................. A61K 9/00 |

OTHER PUBLICATIONS

Chemical Abstracts AN 1994:62289, Koochaki, Dec. 1993.
Database WPI, Week 9414, Derwent Publications Ltd., London, GB; AN 94–111955 & JP A 6 056 675 (Nippon Soda Co) Mar. 1, 1994 [Abstract].

*Primary Examiner*—Keith D. MacMillan
*Attorney, Agent, or Firm*—Ellen Ciambrone Coletti

[57] ABSTRACT

The present invention relates to a composition comprising an antimigraine compound of formula (I) and chitosan, which is particularly suited for intranasal administration.

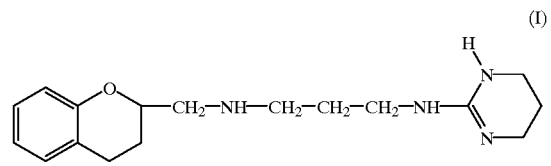

Process for preparing said composition, its use as a medicine and a nasal spray device, especially a unidose nasal spray device containing said composition.

19 Claims, No Drawings

INTRANASAL ANTIMIGRAINE COMPOSITIONS

CROSS-REFERENCE TO RELATED APPLICATIONS

This is a continuation of application Ser. No. 08/718,529, filed Oct. 8, 1996, now abandoned.

This application is based upon PCT application Ser. No. PCT/EP 95/01302, filed Apr. 10, 1995, which claims priority from European Patent Application Ser. No. 94.200.998.6, filed on Apr. 13, 1994.

The present invention relates to a composition comprising an antimigraine compound of formula (I) and chitosan, which is particularly suited for intranasal administration.

WO 93/17017, published on Sep. 2, 1993, discloses compounds of formula (I), the pharmaceutically acceptable acid addition salts thereof and the stereochemically isomeric forms thereof having selective vasoconstrictive properties.

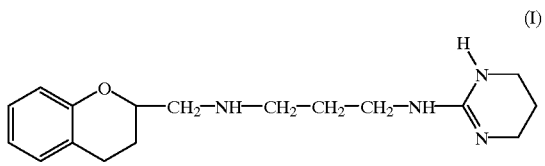

(I)

Among the compounds of formula (I), (−)-(R)-N-[(3,4-dihydro-2H-1-benzopyran-2-yl)methyl]-N'-(1,4,5,6-tetrahydro-2-pyrimidinyl)-1,3-propanediamine and the pharmaceutically acceptable acid addition salts thereof were indicated as the preferred compounds.

In vitro and in vivo animal experiments have demonstrated that N-[(3,4-dihydro-2H-1-benzopyran-2-yl)methyl]-N'-(1,4,5,6-tetrahydro-2-pyrimidinyl)-1,3-propanediamine possesses highly vasoconstrictory properties. The arterial vasoconstrictor response arises through agonistic activation of $5-HT_1$-like receptors. Since excessive cerebral vasodilatation plays a role in migraine, N-[(3,4-dihydro-2H-1-benzopyran-2-yl)methyl]-N'-(1,4,5,6-tetrahydro-2-pyrimidinyl)-1,3-propanediamine has an acute effect in migraine by virtue of its vasoconstrictor effects on cerebral arteries.

Pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term addition salt also comprises the hydrates and solvent addition forms which the compounds of formula (I) are able to form. Examples of such forms are e.g. hydrates, alcoholates and the like.

Preferred acid addition salt form is the hydrochloride, especially the dihydrochloride.

Although in general, oral administration of a drug is considered as most convenient, this route poses particular problems when administering a drug, more in particular an anti-migraine drug, to patients suffering from a migraine attack. Migraine patients often feel nauseous, sometimes resulting in violent vomiting, thus hampering the oral administration of the anti-migraine drug. The successful oral delivery of some anti-migraine substances may also be impeded by its susceptibility to degradation by the acid environment of the stomach and by the digestive activity of several enzymes in the gastrointestinal tract. Other disadvantages of the oral route may be the often poor absorption due to gastroparesis and the extensive first-pass elimination in the liver (the hepatic first-pass effect), whereby a compound is transformed in the liver into a metabolite more prone to excretion. Along with convenient administration, it is essential for an effective treatment of a migraine attack that the activity of the drug sets on immediately, or at least very rapidly, after administration. Hence a means of directly inserting the drug into the bloodstream would be appropriate for the administration of an anti-migraine drug. An obvious way of doing so is by injecting a solution of the drug either intravenously, intramuscularly or subcutaneously. However, the consequent pain, risk of infection, the complex procedures of self-administration and potential for low patient compliance make such parenteral administration undesirable.

The antimigraine compounds of formula (I) are poorly absorbed and are prone to the hepatic first-pass effect.

Intranasal administration appears to be an attractive alternative because it avoids gastro-intestinal degradation and the hepatic first-pass effect and it allows for convenient and simple self-administration. However, the person skilled in the art of pharmaceutical formulations is faced with the problem of preparing a composition which allows intranasal administration of a compound of formula (I) while maintaining the activity of the active ingredient. Furthermore high bioavailability, a rapid onset, and a lack of adverse side-effects due to intranasal administration are required of said composition.

It was found that the composition of the present invention comprising a therapeutically effective amount of a compound of formula (I) and chitosan or a pharmaceutically acceptable salt thereof solves these problems.

U.S. Pat. No. 4,946,870 teaches delivery systems comprising chitosonium polymers and covalent chitosan derivatives and providing a non-irritating substantive gas permeable film that delivers the active ingredient topically. WO 90/09780, published on Sep. 7, 1990 teaches the use of a polycationic substance such as chitosan to enhance the absorption of high molecular weight material such as proteins and peptides across mucosal surfaces, such as the vagina, colon or the nasal cavity. WO 93/15737, published on Aug. 19, 1993 discloses compositions for nasal administration of a number of specific polar metabolites of opioid analgesics comprising absorption promoting agents, such as chitosan.

The composition subject to the present invention differs from the prior art in that the antimigraine compound (not being a protein or a peptide) is delivered in a systemic manner and with a release profile which is suitable to bring expedient relief to antimigraine patients.

Chitosan is partially deacetylated chitin, or poly-N-acetyl-D-glucosamine. The source of the chitin is usually crab shells or shrimp shells. The general formula of chitosan is $(C_6H_{11}O_4N)_n$. The interesting pharmaceutically acceptable salt forms of chitosan are the hydrochloride, lactate, glutamate, maleate, acetate, formate, propionate, malate, malonate, adipate, succinate and the nitrate salt forms. Preferred acceptable salt forms of chitosan are the hydrochloride, lactate, glutamate, maleate and the acetate salt forms.

Different grades of chitosan can be distinguished dependent upon the deacetylation grade. Said deacetylation grade of chitosan may range from 40% up to 90%. The deacetylation grade of chitosan according to the present invention is particularly more than about 70% and preferably more than about 80%.

Another important parameter of chitosan is its molecular weight. As a measure for the molecular weight the viscosity of a 1% solution in 1% acetic acid in water is used. The preferred molecular weight according to the present invention results in a viscosity ranging from 10 to 300 mPa.s, especially from 20 to 200 mPa.s, more particularly from 50 mpa.s to 100 mPa.s. When using chitosan with a molecular weight resulting in a viscosity of a 1% solution in 1% acetic acid in water lower than 10 mPa.s the absorption enhancing effect of chitosan is considered to be strongly reduced. When using chitosan with a molecular weight resulting in a viscosity of a 1% solution in 1% acetic acid in water higher than 200 mPa.s the resulting final composition becomes unsprayable with conventional spraying devices.

The amount of chitosan or the pharmaceutically acceptable acid addition salt thereof in the composition ranges from 0.1% to 5% (w/w), especially especially from 0.1% to 2% (w/w), particularly from 0.3% to 0.7% (w/w), and preferably is about 0.6% (w/w).

If desired, other enhancers may be included in the compositions of the invention such as, for example, phospholipids, e.g. phosphatidylglycerol or phosphatidylcholines; or lysophosphatidyl derivatives, e.g. lysolecithin, lysophosphatidyl-ethanolamine, lysophosphatidylcholine, lysophosphatidylglycerol, lysophosphatidylserine, lysophosphatidic acid. Gelling agents or viscosity-increasing substances may be added. The chitosan may be formulated as microspheres with or without albumin.

The amount of active ingredient may range from 0.1% to 10% (w/w), interesting compositions comprise from 0.1% to 8% (w/w), more interesting compositions comprise from 0.5% to 4% (w/w) of the active ingredient, particular compositions comprise from 0.5% to 2.5% (w/w) of the active ingredient and preferred compositions comprise about 1.25% (w/w) of active ingredient.

The present composition may also contain one or more preservatives selected from quaternary ammonium salts such as lauralkonium chloride, benzalkonium chloride, benzododecinium chloride, cetyl pyridium chloride, cetrimide, domiphen bromide; alcohols such as benzyl alcohol, chlorobutanol, o-cresol, phenyl ethyl alcohol; organic acids or salts thereof such as benzoic acid, sodium benzoate, potassium sorbate, parabens; or complex forming agents such as EDTA.

The amount of preservatives may range from 0.001% to 0.1% (w/w). Preferred compositions comprise about 0.01% (w/w) of one or more preservatives.

The composition may further comprise an appropriate acid selected from the group consisting of hydrochloric acid, lactic acid, glutamic acid, maleic acid, acetic acid, formic acid, propionic acid, malic acid, malonic acid, adipic acid, succinic acid or nitric acid to form an interesting acid addition salt form of chitosan.

Preferred acid is glutamic acid, thus forming chitosan glutamate. It was found that the composition comprising chitosan glutamate was preferred from the view point of tolerability. Tolerabilty is a parameter for indicating the lack of minor adverse effects, such as irritance, bad taste and the like.

The amount of said acid may range from 0.01% to 4% (w/w). Preferred compositions comprise about 0.4% (w/w) of said acid.

Tonicity adjusting agents such as sodium chloride, glucose, dextrose, mannitol, sorbitol, lactose and the like may also be added. Their amount is dependent upon the concentration of the other excipients. The tonicity of the composition should approximately be equal to the tonicity of blood.

The bulk of the composition is water, preferably demineralised water.

The pH range in which chitosan or its salts is soluble depends upon the deacetylation grade of the chitosan. The less the deacetylation grade of the chitosan the higher the pH can be at which the chitosan remains soluble.

The pH of the composition according to the present invention may range from 3.0 to 10, the pH of the composition comprising the preferred form of chitosan may range from 3.0 to 7.0. The more interesting pH range of the composition is from 4.0 to 6.0. The preferred range of pH is between 4.0 and 5.5. When the pH is too high, i.e. the pH is higher than about 7, the composition comprising the preferred from of chitosan becomes turbid. In alkaline media chitosan, especially the preferred form of chitosan, becomes insoluble. A pH below 3 may cause nasal irritation.

The present compositions may be prepared by mixing the active ingredient, the chitosan nd the other excipients in water.

An important feature of the present intranasal composition is its sprayability, i.e. the ability of the composition to form an aerosol. This ability mainly depends upon the viscosity of the composition. When the composition is too viscous, the composition will not allow the formation of a spray. The composition will form large drops or the composition may form a jet when applying the spray device thus resulting in a high concentration of active ingredient on a small area in the nasal cavity. Such high local concentration usually causes irritation. It is another aspect of this invention that the present inventive composition has the right viscosity. It can be sprayed and still the droplets reside long enough in the nasal cavity to allow for a good availability. The viscosity of the solution may range up to 50 mPa.s.

The compositions may adhere to the mucosa, at least to some extent, and this may facilitate retention of the composition of the mucosa and/or enhance the absorption of the active ingredient.

The compositions can be administered via the nasal route using a nasal spray device, pressurized aerosol cannister or simple instillation means. To avoid overdosing and for hygienic reasons a unidose nasal spray device is preferred.

A further aspect of the invention provides the use of the above composition as a medicine, especially the use for the manufacture of a medicament for treating patients suffering from migraine. Hence, a method of treating a patient suffering from migraine by administering an intranasal composition is provided.

Experimental part

EXAMPLE 1

Chitosan (160 mg) was suspended in demineralised water. Lactic acid (80 mg) was added while stirring until a clear solution was obtained. Benzalkonium chloride (2 mg) was also added. The pH of the solution was brought to 5.5 by adding a 0.01 N solution of sodium hydroxide. The active ingredient, i.e N-[(3,4-dihydro-2H-1-benzopyran-2-yl)methyl]-N'-(1,4,5,6-tetrahydro-2-pyrimidinyl)-1,3-propanediamine dihydrochloride was dissolved in the stirred solution. Demineralised water was added to obtain a final volume of 20 ml. Sodium chloride was added until the solution became isotonic with blood.

The solution is stored in small vials of about 125 µl. These vials are adapted to fit into 1 unidose spraying device which delivers about 100 µl of solution.

In the examples hereinafter "Active Ingredient" means (−)-(R)-N-[(3,4-dihydro-2H-1-benzopyran-2-yl)methyl]-N'-(1,4,5,6-tetrahydro-2-pyrimidinyl)-1,3-propanediamine dihydrochloride.

EXAMPLE 2

A test formulation having the following composition was prepared according to an analogous preparation method as described in example 1

Composition 1

| | amount in mg | % (w/w) |
|---|---|---|
| active ingredient | 12.414 mg | 1.24 |
| sodium hydroxide | q.s. ad pH 5.5 | q.s. ad pH 5.5 |
| chitosan | 6 mg | 0.6 |
| benzalkonium chloride | 0.1 mg | 0.01 |
| lactic acid | 4 mg | 0.4 |
| sodium chloride | 5 mg | 0.5 |
| demineralized water | q.s. for 1000 µl | q.s. 100% |

The pH of the above solution is 5.5±0.5

EXAMPLE 3

A double-blind, randomized, cross-over trial in healthy volunteers during four treatment days were set up. All volunteers (n=8) participated in the four sessions of the trial, in which the above formulation was tested. On each treatment day volunteers received a single intranasal administration of 1 mg of a formulation of (−)-(R)-N-[(3,4-dihydro-2H-1-benzopyran-2-yl)methyl]-N'-(1,4,5,6-tetrahydro-2-pyrimidinyl)-1,3-propanediamine dihydrochloride as described in example 1. Unidose nasal sprayers at a concentration of 10 mg/ml, which provided a volume of 100 µl per spray were used. The composition was administered to the volunteers as a single spray in one nostril. Blood was sampled over 24 hours for pharmacokinetic analysis. Venous 10 ml blood samples for drug analysis were taken at 0, 5, 10, 20, 30, 60, 90, 120, 240 and 360 minutes and 24 hours after drug administration. The blood samples were transferred to heparinized tubes and centrifuged within 30 minutes after collection. Separated plasma was transferred to polystyrene tubes adequately labelled with the trial number, subject number and initials, time and date of sampling.

Concentrations of (−)-(R)-N-[(3,4-dihydro-2H-1-benzopyran -2-yl)methyl]-N'-(1,4,5,6-tetrahydro-2-pyrimidinyl)-1,3-propanediamine dihydrochloride were determined by radio immunoassay.

A mean bioavailability of about 35% was found on the basis of the above experiment. (Bioavailability in percent is defined as the amount of active ingredient found in blood plasma after intranasal administration of the active ingredient compared with the amount of active ingredient in blood plasma after intravenous administration.)

EXAMPLE 4

A formulation including lysophospatidylcholine was prepared according to an analogous preparation method as described in example 1

Composition 2

| | % (w/w) |
|---|---|
| active ingredient | 1.24 |
| sodium hydroxide | q.s. ad pH = 5.5 |
| lysophospatidylcholine | 0.50 |
| sodium chloride | 0.50 |
| benzalkonium chloride | 0.01 |
| chitosan | 0.6 |
| lactic acid | 0.4 |
| demineralized water | q.s. 100% |

The pH of the above solution is 5.5±0.5

EXAMPLE 5

The following compositions were also prepared according to the preapration as described in example 1.

| | Composition No. | | | | |
|---|---|---|---|---|---|
| | 3 % (w/w) | 4 % (w/w) | 5 % (w/w) | 6 % (w/w) | 7 % (w/w) |
| active ingredient | 0.12 | 0.496 | 1.986 | 2.48 | 1.24 |
| sodium hydroxide | q.s. ad pH = 4 | q.s. ad pH = 4 | q.s. ad pH = 4 | q.s. ad pH = 4 | q.s. ad pH = 5.5 |
| sodium chloride | 0.9 | 0.8 | 0.5 | 0.4 | 0.6 |
| benz-alkonium chloride | 0.01 | 0.01 | 0.01 | 0.01 | 0.0125 |
| chitosan glutamate | 0.5 | 0.5 | 0.5 | 0.5 | 0.5 |
| demineral-ized water | q.s. 100% | q.s. 100% | q.s. 100% | q.s. 100% | q.s. 100% |
| pH | 4 ± 0.5 | 4 ± 0.5 | 4 ± 0.5 | 4 ± 0.5 | 5.5 ± 0.5 |

Compositions 2 to 7 all appear to show an appropriate release profile and bioavailability.

We claim:

1. An aqueous pharmaceutical composition suitable for administration as a nasal spray which consists essentially of a compound of formula (I),

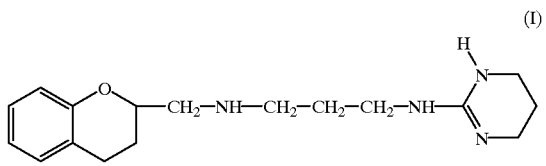

(I)

a pharmaceutically acceptable acid addition salt thereof or a stereochemically isomeric form thereof; chitosan or a pharmaceutically acceptable acid addition salt form thereof and other pharmaceutically acceptable excipients, the bulk of said composition being water wherein chitosan is present in an amount ranging from 0.1% to 5% (w/w).

2. A composition according to claim 1 wherein the compound is (−)-(R)-N-[(3,4-dihydro-2H-1-benzopyran-2-yl)methyl]-N'-(1,4,5,6-tetrahydro-2-pyrimidinyl)-1,3-propanediamine dihydrochloride.

3. A composition according to claim 1 wherein the pH of said composition ranges from 3.0 to 7.0.

4. A composition according to claim 1 wherein the deacetylation grade of the chitosan used in the composition is more than about 70%.

5. A composition according to claim 1 wherein the pharmaceutically acceptable acid addition salt form of chitosan is the hydrochloride, lactate, glutamate, maleate, acetate, formate, propionate, malate, malonate, adipate, succinate or nitrate.

6. A composition according to claim 1 wherein the pharmaceutically acceptable acid addition salt form of chitosan is chitosan glutamate.

7. A nasal spray device containing a composition as claimed in claim 1.

8. A method for treating patients suffering from migraine which comprises intranasally administering to such patients the pharmaceutical composition of claim 1.

9. A method for treating patients suffering from migraine which comprises intranasally administering to such patients the pharmaceutical composition of claim 2.

10. A method for treating patients suffering from migraine which comprises intranasally administering to such patients the pharmaceutical composition of claim 3.

11. A method for treating patients suffering from migraine which comprises intranasally administering to such patients the pharmaceutical composition of claim 4.

12. A method for treating patients suffering from migraine which comprises intranasally administering to such patients the pharmaceutical composition of claim 5.

13. A method for treating patients suffering from migraine which comprises intranasally administering to such patients the pharmaceutical composition of claim 6.

14. A composition according to claim 1, wherein the viscosity of the composition ranges up to 50 mPa.s.

15. A composition according to claim 1, wherein chitosan is present in an amount ranging from 0.1% to 2% (w/w).

16. A composition according to claim 15, wherein chitosan is present in an amount ranging from 0.3% to 0.7% (w/w).

17. A composition according to claim 16, wherein chitosan is present in an amount of about 0.6% (w/w).

18. A composition according to claim 1 wherein the composition is in the form of a solution.

19. A method for treating patients suffering from migraine which comprises intranasally administering to such patients the pharmaceutical composition of claim 18.

* * * * *